(12) United States Patent
Castillo

(10) Patent No.: US 11,731,949 B2
(45) Date of Patent: Aug. 22, 2023

(54) APPARATUS FOR DECARBOXYLATION OF CANNABIS EXTRACTS

(71) Applicant: Jenny's Rose, LLC, Los Angeles, CA (US)

(72) Inventor: James Castillo, San Diego, CA (US)

(73) Assignee: Jenny's Rose, LLC, Los Angeles, CA (US)

( * ) Notice: Subject to any disclaimer, the term of this patent is extended or adjusted under 35 U.S.C. 154(b) by 154 days.

(21) Appl. No.: 16/844,673

(22) Filed: Apr. 9, 2020

(65) Prior Publication Data

US 2021/0317101 A1 Oct. 14, 2021

(51) Int. Cl.
| | |
|---|---|
| *C07D 311/80* | (2006.01) |
| *B01J 6/00* | (2006.01) |
| *B01D 3/02* | (2006.01) |
| *B01D 5/00* | (2006.01) |
| *A61K 36/185* | (2006.01) |

(52) U.S. Cl.
CPC .............. *C07D 311/80* (2013.01); *B01J 6/008* (2013.01)

(58) Field of Classification Search
CPC .......... C07D 311/80; B01J 6/008; B01D 3/02; B01D 5/006; B01D 5/009; A61K 2236/00; A61K 36/185
See application file for complete search history.

(56) References Cited

U.S. PATENT DOCUMENTS

| | | | | |
|---|---|---|---|---|
| 8,445,034 | B1 * | 5/2013 | Coles, Jr. .............. | A61K 31/192 424/725 |
| 9,351,953 | B2 | 5/2016 | Stodola | |
| 10,195,159 | B2 | 2/2019 | Whittle et al. | |
| 10,471,113 | B1 | 11/2019 | Castillo | |
| 2011/0046213 | A1 * | 2/2011 | Bhatarah ................... | A61P 1/08 514/454 |
| 2018/0296616 | A1 | 10/2018 | Rivas | |
| 2018/0339973 | A1 * | 11/2018 | Changoer .......... | B01D 11/0288 |

FOREIGN PATENT DOCUMENTS

| | | |
|---|---|---|
| WO | 2016179247 A1 | 11/2016 |
| WO | WO-2016179247 | 11/2016 |
| WO | 2018187500 A1 | 11/2018 |
| WO | 2019090428 A1 | 5/2019 |
| WO | WO-2019090428 | 5/2019 |
| WO | 2019211797 A1 | 11/2019 |
| WO | WO-2019211797 | 11/2019 |
| WO | 2020197983 A1 | 10/2020 |
| WO | WO-2020197983 | 10/2020 |

OTHER PUBLICATIONS

Ferber, S. G., "The "entourage effect": terpenes coupled with cannabinoids for the treatment of mood disorders and anxiety disorders." Current neuropharmacology 18.2 (2020): 87-96.*
Booth, J. K. "Terpene synthases and terpene variation in Cannabis sativa." Plant physiology 184.1 (2020): 130-147.*
EPO, International Search Report and Written Opinion in co-pending PCT International Patent Application No. PCT/US2021/026721 dated Jul. 12, 2021.
Romano, Luigi et al., "An Overview of Galenic Preparation Methods for Medicinal Cannabis". Current Bioactive Compounds, vol. 15, No. 2, Mar. 12, 2019 (Mar. 12, 2019), pp. 174-195, Paragraph 2.4; figures 1,2.

* cited by examiner

*Primary Examiner* — John M Mauro
(74) *Attorney, Agent, or Firm* — Stefan J. Kirchanski; Matthew J. Spark; Zuber Lawler LLP

(57) ABSTRACT

A controlled decarboxylation of cannabinoids results in a high yield of decarboxylated forms of cannabinoids and also preserves the integrity of volatile components such as terpenoids and as well as fats and lipids that are present in the *cannabis* extract. The inventive apparatus allows the different components in the *cannabis* plant extract to be kept in the same reaction mixture during the decarboxylation process, while allowing the decarboxylation process to proceed without breakdown of the more volatile components of the mixture by use of a very low temperature condenser. The invention also relates to a method for controlled decarboxylation of cannabinoids using the novel apparatus.

4 Claims, 1 Drawing Sheet

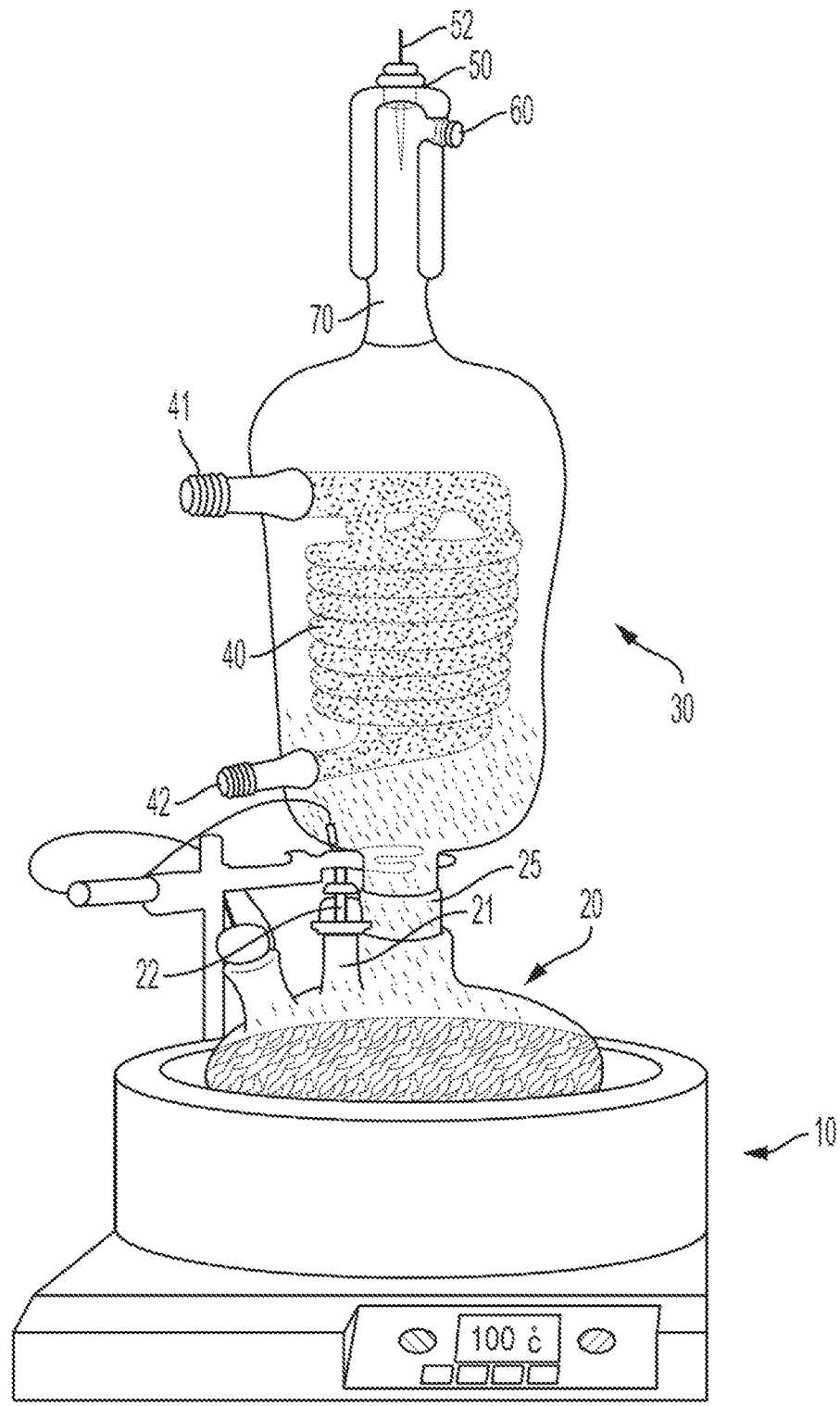

APPARATUS FOR DECARBOXYLATION OF CANNABIS EXTRACTS

CROSS-REFERENCE TO PRIOR APPLICATIONS

Not applicable

U.S. Government Support

Not applicable

BACKGROUND OF THE INVENTION

Area of the Art

The present invention is in the art of processing plant extracts and is more specifically directed to an apparatus for improved decarboxylation of *cannabis* extracts.

Description of the Background Art

The *cannabis* plant (*Cannabis sativa* L.) ("*cannabis*") has a long history use for both medicinal and recreational purposes. *Cannabis* plant material contains a variety of chemical compounds, including those responsible for the "high" associated with *cannabis* consumption as well as other physiological effects. *Cannabis* plants contain a complex mix of cannabinoids, a family of prenylated acylphloroglucinol derivatives that consist of over 100 different distinct chemical entities. Cannabinoids have a variety of different chemical structures, and the modern definition of "cannabinoid" is functional rather than structural: namely, they all are presumed to bind to cannabinoid receptors that are present on a variety of human cells. Cannabinoid receptors are part of a cellular signaling system known as the endocannabinoid system (ECS) and compounds that interact with these receptors can have profound physiological effects including effects on the central nervous system as well as immune system effects.

In addition to cannabinoids, the *cannabis* plant also contains myriad other natural products such as terpenes and other terpenoids, and flavonoids that alter the taste, smell and physiological effect of *cannabis*. Although terpenoids and flavonoids are known to have potential medical and recreational benefits, medical as well as recreational effects of *cannabis* have been generally attributed to cannabinoids. The story is even more complicated because it is becoming recognized that cannabinoids interact with each other as well as with terpenoids and possibly other compounds present in the plant to produce medical and recreational effects that cannot be attributed to cannabinoids alone. This interaction or synergy resulting from the complex mixture of compounds present within the *cannabis* plant is known as the "entourage effect," in which a mixture of compounds from the *cannabis* plant is believed to demonstrate greater efficacy in treating a medical condition than any of its constituent compounds in isolation.

Historically, *cannabis* has been consumed by smoking or ingestion. *Cannabis* resin known as 'hashish' was a well-known product in many countries, particularly in Asia. Hashish is a yellow to brown solid that consists largely of the glandular trichomes that cover *cannabis* inflorescences. The precise spectrum of cannabinoids present in the resin varies greatly from cultivar to cultivar. No matter which cannabinoids a particular cultivar synthesizes, they are essentially all localized in these glandular trichomes. The widespread legalization of medical *cannabis* followed by the legalization of recreational *cannabis* by an increasing number of U.S. states as well as foreign countries is rapidly changing how *cannabis* products are produced and consumed.

The cannabinoids present naturally in the plant are in the acidic form which have few physiological or psychoactive effects. For example, commonly used cannabinoids $\Delta 9$-tetrahydrocannabinol ($\Delta 9$-THC), cannabidiol (CBD), and tetrahydrocannabivarin (THCV) are present naturally in the plant as $\Delta 9$-tetrahydrocannabinolic acid ($\Delta 9$-THC-A), cannabidiolic acid (CBD-A), and tetrahydrocannabivarinic acid (THCV-A), respectively. Decarboxylation from the acid to the active form occurs upon exposure to heat. This can occur when in an uncontrolled manner, for example when the plant material is smoked in a joint or baked in edibles. Uncontrolled decarboxylation in not desirable because it is not possible to predict to what extent the cannabinoids are converted to the physiologically active form. Uncontrolled decarboxylation can also destroy the volatile terpenoids and flavonoids present in the plant materials. Decarboxylation may be accomplished by heating *cannabis* plant extracts at high temperatures. However, to obtain complete or near complete decarboxylation of either the plant material or plant extract, prolonged heating is required. Typically, decarboxylation of cannabinoids is done at high temperatures to maximize yield. However, exposing *cannabis* to high temperature may cause either burning of the plant material or boiling of the solvent in which the extract has been made, and may lead to a breakdown of cannabinoids and volatile components such as terpenoids and flavonoids, for example.

The invention provides an apparatus for decarboxylation, wherein the apparatus can maintain a stable temperature to allow effective decarboxylation of compounds such as cannabinoids, for example. The invention further provides an apparatus for decarboxylation, wherein the apparatus can maintain a stable temperature to allow a cannabinoid mixture to be heated, and any vaporized mixture to be condensed and refluxed in a manner that facilitates decarboxylation of components such as cannabinoids, for example, without allowing the temperature to rise such that the volatile components such as terpenoids and as well as fats and lipids that are present in the extract, are allowed to either break down in the reaction mixture or be lost via evaporation. The invention also provides a method for using the apparatus that would allow for controlled decarboxylation of compounds such as cannabinoids which results in a high yield of the decarboxylated compounds and that also preserves the integrity of volatile components such as terpenoids and as well as fats and lipids that are present in the extract.

In U.S. Pat. No. 10,195,159, ('159 patent), the decarboxylation process is described as yielding a decarboxylated cannabinoid rich fraction, using high temperature, that is also "substantially free of volatile terpenes which may cause stability problems." The '159 patent describes use of temperatures in the range of 175° 200° C. on "high-CBD" material would result in "the isolation of a cannabinoid-rich fraction which is substantially free of terpenes." In case of "high-THC" material, the preference is to use somewhat lower temperatures to limit the conversion of THC to either CBN or delta-8-THC, but even so, the recommended temperatures are in the range of 130°-175° C. In U.S. Pat. No. 10,413,843, the decarboxylation process involves evaporation of the ethanol solvent prior to heating of the *cannabis* extract to 120-140° C. to convert THCA to THC, followed by distillation of the decarboxylated oil to remove terpenes.

Even where the processes seek to capture the terpene fraction, the process relies on separating terpenes and cannabinoids to optimize separation of terpene-rich and cannabinoid-rich fractions. For example, the '159 patent states that since the terpene-rich fraction is more volatile than the cannabinoid rich-fraction, it can be removed in an initial extraction step at a lower temperature. The temperature may then be increased in order to volatilize the cannabinoid-rich fraction.

However, it is increasingly being recognized that the entourage effect of the *cannabis* plant is reliant on the different types of compounds, cannabinoids, terpenes and even some of the waxes and lipids, working together in a synergistic manner, providing greater therapeutic efficacy than any of its constituent compounds in isolation. For example, U.S. patent application Ser. No. 16/596,287, entitled "Therapeutic *Cannabis* Extracts", which was filed on Oct. 8, 2019, discusses the entourage effect and *cannabis* formulations comprising a "remainder" fraction.

Thus, there is a need for an apparatus and method where the different components in the plant extract may be kept in the same reaction mixture during the decarboxylation process, while allowing the decarboxylation process to proceed without breakdown of the more volatile components of the mixture.

Accordingly, there is a need for an apparatus and method for using the same that would allow for controlled decarboxylation of cannabinoids results in a high yield of the decarboxylated forms and that also preserves the integrity of volatile components such as terpenoids and as well as fats and lipids that are present in the reaction mixture and extract.

SUMMARY OF THE INVENTION

In accordance with the invention, provided is a novel apparatus for controlled decarboxylation of cannabinoids. A controlled decarboxylation of cannabinoids results in a high yield of decarboxylated forms of cannabinoids and also preserves the integrity of volatile components such as terpenoids and as well as fats and lipids that are present in the *cannabis* extract. Also provided is a method for controlled decarboxylation of cannabinoids using the novel apparatus. The invention further provides an apparatus and a method where the different components in the *cannabis* plant extract may be kept in the same reaction mixture during the decarboxylation process, while allowing the decarboxylation process to proceed without breakdown of the more volatile components of the mixture.

The inventive apparatus comprises an upper and a lower chamber. The *cannabis* extract is placed in the lower chamber which is heated to a decarboxylating temperature. A condenser in the upper chamber is cooled to a temperature below 0° C. so that volatiles from the lower chamber are condensed and cooled to prevent decomposition whereupon the condensed volatiles fall back into the first chamber.

DESCRIPTION OF THE FIGURES

FIG. 1 is a diagram of the reflux apparatus of the present invention.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a device for controlled decarboxylation of cannabinoids.

Embodiments of the invention are discussed in detail below. In describing embodiments of the invention, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

Traditional Decarboxylation Methods

Decarboxylation of cannabinoids can be accomplished by heating *cannabis* plant extracts at high temperatures (i.e., temperatures above 100° C.) for prolonged periods of time. However, heating at high temperature leads to the breakdown of the cannabinoids and breakdown or loss of volatile components such as terpenoids. Further, uncontrolled decarboxylation of the complex mix of cannabinoids present in the plant may not be desirable where the manufacturer may want to control the composition of the final mixture and obtain a targeted mixture of decarboxylated cannabinoids.

Acidic forms of cannabinoids are generally physiologically inactive but can be readily decarboxylated into biologically active molecules. Decarboxylation is a function of time and temperature: at higher temperatures decarboxylation occurs in a relatively short period of time, whereas at lower temperatures decarboxylation takes longer. In this regard, manufacturers may apply different combinations to time and temperature to optimize their yield, but it is recognized that the goal of the decarboxylation process is to facilitate the production of high concentration of decarboxylated cannabinoids in the final product, at the expense of other compounds, such as terpenes that may be present in the extract. For example, it is believed that THC-A may be decarboxylated to THC when heated at 100° C. for 3 hours. Whereas, THC-A may be decarboxylated to THC when heated at 98° C. for 4 hours, or when heated above 160° C. for 10 minutes. When heated at 200° C., THCA may be decarboxylated within seconds. However, using high temperature for decarboxylation may also increase the rate of conversion of THC to CBN. It is believed that degradation of THC to CBN can be considerable even at temperatures between 85-100° C. Iffland K et al., European Industrial Hemp Association, October 2016. This breakdown is not desirable where the manufacturer is targeting the conversion of THCA to THC and CBN is an unwanted byproduct of the reaction mixture.

Apparatus for Controlled Decarboxylation of Cannabinoids

The invention describes a novel reflux apparatus and a method for controlled decarboxylation of cannabinoids that also prevents breakdown of the cannabinoids and volatile components such as terpenoids, flavonoids, and desirable plants lipids and waxes that may be present in the reaction mixture, for example.

The method of the invention allows for controlled decarboxylation of cannabinoids by heating a mixture comprising cannabinoids at 80° C.-120° C. in a novel reflux apparatus. The reflux apparatus is illustrated in FIG. 1. The reflux apparatus is comprised of a lower chamber 20 that holds a mixture comprising the reaction mixture. The reaction mixture comprises *cannabis* plant extract containing non-decarboxylated (i.e., acidic form) of naturally occurring cannabinoids, terpenoids, and other desirable plant materials. The lower chamber 20 is normally placed on or in a heat source 10. Lower chamber 20 may further comprise an outlet 21 to insert a thermometer, thermistor or similar temperature sensor 22. The temperature sensor 22 may be used to monitor the temperature of the lower chamber 20 and maintain it between 80° C.-120° C. Lower chamber 20 is connected to an upper chamber 30 via a short-neck 25. Upper chamber 30 includes a spiral (or other configurations known to one of skill in the art to increase surface area) cooling core 40, which circulates coolant to maintain a lower temperature in the upper chamber 30 in order to condense vapor in upper chamber 30. Cooling core 40 is connected via connecters 41 and 42 to a coolant reservoir (not shown). The upper chamber 30 may further comprise an outlet 50 for inserting a second temperature sensor 52 (thermometer, thermistor, etc.) and an outlet connector 60, which may optionally be used to connect, for example, to a distillation apparatus. In the absence of an added distillation apparatus, the outlet connector 60 may function as a safety valve. The second temperature sensor 52 can be used to monitor the temperature of vapor in the upper chamber 30.

The method of the invention includes heating a mixture comprising cannabinoids at 80° C.-120° C. in a novel reflux apparatus. In one embodiment, the heater 10 is a water bath set at a constant temperature of between 80° C.-120° C. Heating the mixture in the lower chamber 20 results in vaporization of volatile components in the mixture, which then condense upon contact with the cooling core 40 in the upper chamber 30. Upon condensation, the liquid travels back to the lower chamber 20.

In one embodiment, the cooling core 40 is cooled by a coolant such as propylene glycol. In one aspect, the coolant is circulated into upper chamber 30 via coolant reservoir (not shown) which typically includes a refrigeration system and a pump. In one embodiment, the coolant is chilled to maintain the temperature of the coolant below about −30° C. to −40° C. It is generally known in the art of *cannabis* extraction to cool a vapor stream to allow refluxing. However, it is not known that chilling the cooling core to below 0° C. results in superior retention of volatiles and lack of cannabinoid decomposition. It is surprising that lowering the cooling core temperature while keeping the bulk decarboxylating temperature in the lower chamber 20 the same reduces cannabinoid decomposition.

In one embodiment, the lower chamber 20 is connected to the upper chamber 30 via a short-neck 25 comprising a male 24/40 joint. In one embodiment, the upper chamber 30 is about 1.5 feet tall and about 6 inches in diameter. The upper chamber 30 contains the spiral cooling core 40. In one embodiment, the cooling core 40 is about 6 inches tall and about 3 inches in diameter. The cooling core 40 is connected via connecters 41 and 42 to a coolant reservoir (not shown). In one embodiment, connecters 41 and 42 are ¼ inch in size to which are connected flexible hoses leading to the cooling reservoir. In one embodiment, the top connection 70 of upper chamber 30 may comprise a female 24/40 joint. The upper chamber 30 may further comprise an outlet connector/safety valve 60, which may optionally be used to connect to a distillation apparatus. In one embodiment, the outlet connector/safety valve 60 comprises a female 24/40 joint.

Controlled Decarboxylation of Cannabinoids

Decarboxylation is achieved by refluxing the *cannabis* extract ("oil"). For this purpose the extract is diluted with alcohol (ethanol) to reduce its viscosity. Usually s given volume of extract is diluted to a volume of about 120% (for example, a volume of 80 ml of extract is diluted with 26 ml of alcohol). Then, water equal to about 3-5% of the diluted volume is added. For example, 5% of 96 ml is 4.8 ml so 4.8 ml of water is added. Table 1 shows the cannabinoid profile of an extract prior to decarboxylation. Effective decarboxylation of cannabidiolic acid (CBD-A) to cannabidiol (CBD) or delta-9-tetrahydrocannabidiolic acid (Δ9-THC-A) to delta-9-tetrahydrocannabidiol (Δ9-THC) was achieved after refluxing the diluted mixture at 80° C. for two hours. Following refluxing, the diluted solution was subjected to rotary evaporation until substantially all alcohol and water in the mixture had been removed.

TABLE 1

Cannabinoid process of extract prior to decarboxylation

| Analyte | % | mg/g |
|---|---|---|
| THC-A | 0.91 | 9.1 |
| Δ9-THC | 1.90 | 19.0 |
| CBD-A | 52.83 | 528.3 |
| CBD | 20.31 | 203.1 |
| CBN | None Detected | None Detected |
| CBG-A | 1.05 | 10.5 |
| CBG | 0.46 | 4.6 |

Decarboxylation of cannabinoids into the psychoactive form was confirmed by chromatography, as shown in Table 2. The decarboxylation was complete. Furthermore, refluxing the mixture at 80° C. for two hours did not result in conversion of THC to CBN in any significant amount as compared to the starting material.

TABLE 2

Cannabinoid profile of decarboxylation product

| Analyte | % | mg/g |
|---|---|---|
| THC-A | None Detected | None Detected |
| Δ9-THC | 2.55 | 25.5 |
| CBD-A | None Detected | None Detected |
| CBD | 64.97 | 649.7 |
| CBN | 0.09 | 0.9 |
| CBG-A | None Detected | None Detected |
| CBG | 1.28 | 12.8 |

It will be appreciated that decarboxylation with the apparatus results in very effective and complete decarboxylation in a relative short period of time with no appreciable decomposition of cannabinoids. If there had been appreciable decomposition, an increased amount of CBN should have been apparent.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method of producing decarboxylated cannabinoids comprising the steps of heating cannabis plant extract in a first chamber to a temperature between of about 80° C. and about 120° C., and allowing vaporized cannabis plant extract to escape into a second chamber fluidically connected to the first chamber where the vaporized cannabis plant extract is condensed by a condenser chilled below 0° C. and is returned to the first chamber.

2. The method of producing decarboxylated cannabinoids of claim 1 wherein the second chamber connected to the first chamber is a condenser, wherein a coolant temperature below 0° C. circulates.

3. The method of producing decarboxylated cannabinoids of claim 1, wherein the coolant temperature is about −30° C. to −40° C.

4. The method of producing decarboxylated cannabinoids of claim 1, wherein the condenser is chilled to between about −30° C. and −40° C.

* * * * *